(12) United States Patent
Marks

(10) Patent No.: US 8,800,352 B2
(45) Date of Patent: Aug. 12, 2014

(54) METHOD FOR AUTOMATIC OPTIMIZATION OF LIQUID CHROMATOGRAPHY AUTOSAMPLER

(75) Inventor: Aaron N. Marks, Northborough, MA (US)

(73) Assignee: Thermo Finnigan LLC, San Jose, CA (US)

(*) Notice: Subject to any disclaimer, the term of this patent is extended or adjusted under 35 U.S.C. 154(b) by 284 days.

(21) Appl. No.: 13/212,070

(22) Filed: Aug. 17, 2011

(65) Prior Publication Data
US 2013/0014566 A1 Jan. 17, 2013

Related U.S. Application Data

(60) Provisional application No. 61/508,488, filed on Jul. 15, 2011.

(51) Int. Cl.
*G01N 13/00* (2006.01)
(52) U.S. Cl.
USPC .......................................................... 73/61.55
(58) Field of Classification Search
CPC ............................... G01N 30/24; G01N 30/34
USPC .......................................... 210/659; 73/61.55
See application file for complete search history.

(56) References Cited

U.S. PATENT DOCUMENTS

| | | | |
|---|---|---|---|
| 3,909,203 A | 9/1975 | Young et al. | |
| 3,954,012 A | 5/1976 | Christen et al. | |
| 3,960,003 A | 6/1976 | Beyer et al. | |
| 3,960,020 A | 6/1976 | Gordon et al. | |
| 4,276,260 A | 6/1981 | Drbal et al. | |
| 4,323,537 A | 4/1982 | Mody | |
| 4,429,584 A | 2/1984 | Beyer et al. | |
| 4,468,331 A * | 8/1984 | Antle et al. | 210/659 |
| 4,541,291 A | 9/1985 | Churchill et al. | |
| 4,713,974 A | 12/1987 | Stone | |
| 4,939,943 A | 7/1990 | Strohmeier | |
| 4,969,993 A | 11/1990 | Nash, Jr. et al. | |

(Continued)

FOREIGN PATENT DOCUMENTS

WO    WO 2006/089103 A1    8/2006

OTHER PUBLICATIONS

Y. Wang, "Autosampler Programming for Improved Sample Throughput in Liquid Chromatography/Mass Spectrometry," Clinical Chemistry, vol. 51 (11), 2005, pp. 2216-2218.

*Primary Examiner* — Peter Macchiarolo
*Assistant Examiner* — Alex Devito
(74) *Attorney, Agent, or Firm* — Thomas F. Cooney

(57) ABSTRACT

An method for optimizing operation of an autosampler coupled to a liquid chromatography (LC) system comprises: reading, from electronic memory storage, a pre-injection time corresponding to the time required for the autosampler to perform operations preparatory to injecting a sample; calculating an autosampler delay time from the pre-injection time and from a sample analysis time; performing the autosampler operations preparatory to injecting the sample after delaying said autosampler operations for the autosampler delay time; measuring a time value for the preceding performing of autosampler operations; replacing the pre-injection time value stored on the electronic memory storage with the measured time value for the preceding performing of autosampler operations if the measured value is greater than the pre-injection time value stored on the electronic memory storage; and injecting the sample from the autosampler into the LC system after receipt of a signal from the LC system by the autosampler.

16 Claims, 12 Drawing Sheets

(56) References Cited

U.S. PATENT DOCUMENTS

| | | |
|---|---|---|
| 5,005,434 A | 4/1991 | Watanabe et al. |
| 5,204,269 A | 4/1993 | Barker et al. |
| 5,814,742 A | 9/1998 | Vissers et al. |
| 5,948,360 A | 9/1999 | Rao et al. |
| 6,143,573 A | 11/2000 | Rao et al. |
| 6,635,173 B2 | 10/2003 | Brann |
| 6,770,876 B2 | 8/2004 | Gu et al. |
| 6,802,228 B2 | 10/2004 | Liang |
| 7,588,725 B2 | 9/2009 | Ozbal et al. |
| 2009/0145205 A1 | 6/2009 | Hochgraeber et al. |

* cited by examiner

METHOD FOR AUTOMATIC OPTIMIZATION OF LIQUID CHROMATOGRAPHY AUTOSAMPLER

TECHNICAL FIELD

This invention pertains generally to liquid chromatography, and more particularly to methods for automatically operating an apparatus for delivering samples of liquid to be analyzed in a liquid chromatographic column.

BACKGROUND OF THE INVENTION

In liquid chromatography, a compound is broken down into its components in a chromatographic column, so that these components can be further processed or analyzed by a detector, such as a mass spectrometer. In various liquid chromatography techniques, such as High-Pressure Liquid Chromatography (HPLC), the components of a sample to be separated or analyzed are dissolved in a mobile phase liquid, termed an eluent, and then conveyed by that liquid to a stationary phase within one or more chromatography columns. HPLC analyses are employed in a wide variety of applications, such as drug discovery and development, environmental testing, and diagnostics. In HPLC systems, the chromatographic columns are interconnected to other components by fluidic systems. Such fluidic systems generally include an injection valve, possibly one or more auxiliary valves, various solvent and wash fluid reservoirs, together with various interconnecting fluid tubing lines which are used. Such a fluidic system may be used to supply the liquid, with dissolved sample, to a chromatographic column, and to transfer chromatographically separated dissolved components from the column to, for example, a detector. Selected pressures ranging from substantially atmospheric pressure to pressures on the order of ten thousand pounds per square inch are common in HPLC systems to force the liquid into the column. A detector interfaced to a chromatography system may analyze various samples in serial fashion.

In many situations, there is a need to analyze a large number of samples by HPLC in an efficient manner. To facilitate efficient sample selection and processing, automated analysis systems are available which usually include automatic sample injectors or auto-injectors. Such auto-injectors, often referred to as autosamplers, hold a plurality of samples to be analyzed and are able to feed these in series into a liquid chromatographic analysis system. Typical auto-injectors include a plurality of sample reservoirs, a syringe or syringe-like sample transport system, and automation and computer control systems. The auto-injector system may also include the fluidic system components—the valves, fluid reservoirs, and interconnecting fluid tubing lines—described in the previous paragraph. Auto-injectors commonly mimic cumbersome manual injection methods in which a metered aliquot of a sample is aspirated from a desired sample reservoir into a transfer tubing loop under the action of a syringe pump. The aspiration process is often controlled by pulling back on a plunger or piston to create a negative pressure resulting in aspiration of the sample. Upon reconfiguration of the valve of valves of the fluidic system, the sample may then be transferred to the column. The term "autosampler" is sometimes used to refer to just the aspiration and sample transport portion of such a system.

FIGS. 1A-1B illustrate a known chromatography analysis system including an auto-injector, adapted from that described in United States Patent Application Publication US2009/0145205-A1, in the name of inventor Hochgraeber and incorporated herein by reference. FIG. 1A illustrates the system with the high pressure valve 1 configured in a LOAD position and FIG. 1B illustrates the same system with the valve configured in an INJECT position. The valve has six fluid ports, shown as ports 11, 12, 13, 14, 15 and 16. A high-pressure pump 40 that can supply a constant flow rate of solvent (supplied from a not-illustrated solvent reservoir) under high pressure is connected to port 15. In the switching position of the valve as drawn in FIG. 1A, this flow reaches port 14 through groove 25 of the valve 1, and then reaches a chromatographic column 41. A sample aspiration device, such as sample needle 44, is configured so as to dip into and withdraw a portion of sample from a sample container 43. The sample needle 44 is fluidically connected to port 12 of the valve 1. Instead of being moved into sample container, sample needle 44 can be moved into a waste container 38 to dispose of excess liquid. The needle may be directed so as to access various sample containers 43 or waste containers 38 under the operation of a computer controlled mechanical robot device 39, such as a robotic arm and supporting structures.

Typically, the robot device 39 is operable so as to controllably and automatically position the needle 44 over any of the sample containers 43, waste containers 38, or other containers or ports. The robot device is typically also operable so as to vertically dip the sample needle 44 into a sample container 43 so as withdraw a sample portion and to subsequently lift the sample needle out of the sample container. A syringe or syringe pump 42 for drawing sample liquid is connected to port 11 of valve 1. The two remaining ports 13, 16 are externally connected to one another via a sample loop 50. Sample fluid can thereby be drawn from sample container 43 into sample loop 50 with the aid of syringe or syringe pump 42. The switching position of the valve as drawn is referred to as the LOAD position, since the sample material is being loaded into the sample loop.

In order to feed the sample material into the high-pressure liquid stream, the valve 1 is switched over to a second switching position, which is shown in FIG. 1B. In this configuration, sample loop 50 is looped into the liquid path between pump 40 and column 41. The sample liquid previously drawn into sample loop 50 is thereby transported with the liquid stream coming from pump 40 into column 41, where the chromatographic separation takes place. A detector 45, commonly a mass spectrometer, may be connected downstream of the column. The switching position of the valve as drawn is referred to as the INJECT position, since the sample material is being injected into the high-pressure liquid. The entire process may be repeated for a subsequent sample. Although the sample containers 43 are illustrated, in FIGS. 1A-1B, as glass vials, they could alternatively comprise wells of microtiter plates or any other form of sample container. Sample reservoirs may be sealed with a plastic film or metal foil, or a septum.

FIG. 2 illustrates another known chromatography analysis system including a different commonly-used auto-injector configuration. The system shown in FIG. 2 comprises a separate modular autosampler system 2 that comprises aspiration, transfer and dispense capabilities. The robot system 39 of the autosampler system 2 shown in FIG. 2 is operable so as to aspirate a portion of sample from any one of the sample containers 43 and then dispense the sample portion to a sample injection port 7 of a modular chromatography system 9. The illustration shown in FIG. 2 is schematic; typically, the injection port 7 may be configured so that the sample needle 44 may be inserted into the injection port to as to form a leak-tight seal therebetween during injection of the sample portion. As in the chromatography systems shown in FIG. 1, the system of FIG. 2 comprises a multi-port valve 1. However, the fluid connections of the system of FIG. 2 are plumbed differently from those of the system of FIG. 1 partly because the syringe pump 42 is a component of the autosampler module 2. The valve configuration shown in FIG. 2 is a LOAD configuration in which the sample introduced into injection port 7 is delivered to sample loop 50. With this configuration, any fluid previously in the sample loop 50 is flushed out to waste container 8. In an alternative ELUTE configuration (not illustrated in FIG. 2), the grooves 21, 23, 25 of the valve 1 are re-aligned, by rotation of a rotor of the valve, such that a buffer solution or other solvent is caused to pass through the sample loop 50 under high pressure conditions provided by pump 40, such that the previously loaded sample portion is flushed, together with the buffer or solvent, out of the loop 50 and into column 41.

The auto-injector systems illustrated in FIGS. 1-2 are basic systems which provide limited fluid-routing flexibility and limited ability to change solvents during the course of a separation. More-complex systems are known—comprising one or more additional valves, fluid reservoirs or columns—which provide additional necessary or required functionality. For instance, U.S. Pat. No. 7,588,725, in the names of inventors Ozbal et al. and incorporated herein by reference, teaches an autoinjection system having a sample injection valve, a column control valve and a wash control valve. The sample injection valve has a first position which applies a reduced pressure to a sample sipper tube for aspirating a fluidic sample into the sample sipper tube, and a second position which delivers the fluidic sample to a sample supply loop. The column control valve has a first position which delivers the fluidic sample from the sample supply loop to a sample chromatography column, and a second position which reverses direction of fluid flow through the sample chromatography column to deliver the fluidic sample to a sample analyzer. The wash control valve has a first position which supplies a wash buffer solution to the sample chromatography column in a forward fluid flow direction, and a second position which supplies elution solvent to flush the sample supply loop. Fluidic circuits taught by Ozbal et al. provide the capability of passing a fluid over the insoluble matrix of a chromatography column in a first direction such that an analyte in the fluid binds to the insoluble matrix, and back-eluting an elution fluid over the insoluble matrix in a second direction opposite the first direction to output a sample that includes the analyte. Fluidic circuits taught by Ozbal et al. provide the capabilities of delivering wash buffer solution from the wash control valve to the sample chromatography column; delivering elution solvent from the wash control valve to the sample supply loop and aspirating a second sample fluid while simultaneously outputting a first fluid in the sample loop to an analyzer.

U.S. Pat. No. 6,635,173, in the name of inventor Brann and incorporated herein by reference discloses a multi-column chromatography system which is illustrated herein as FIG. 3 of the present document. As can be seen therein, the system 50 contains an autosampler 51 which includes a plurality of injection valves 54, a plurality of pumps 56, a plurality of columns 58, and a selector valve 60 and a detector 62. Columns 58 may comprise a wide variety of columns useful for chromatographic analysis which can be used to direct a fluid sample into the entrance orifice of a given detector. For example, columns 58 may comprise high performance HPLC columns, capillary electrophoresis columns, gas chromatography columns, flow injection transfer lines, etc. In addition, although not shown, the system may also preferably include a port valve, positioned before the columns, which in the case of a single column system (one or more pumps and one or more columns) operates to load sample in one direction and elute in the opposite direction, as previously described in this document. In the case of a two column system, the port valve provides a similar function, and also provides a loop for eluting solvent.

Each combination of pump 56, injection valve 54, and column 58 (together with any associated tubing, additional valves, additional pumps or additional columns) shown in FIG. 2 may be regarded as a separate chromatographic system operating in parallel with three other such chromatographic systems. In that regard, it can be appreciated that each chromatographic system is controlled by the computer controller 63 to ensure that samples are introduced by the autosampler to avoid overlap at the detector end, and to ensure maximum use of the detector's time as a detector. In that regard, the system 50 may be considered as comprising four (4) independent chromatography systems, wherein each system contains one (1) or more pumps and one (1) or more columns. Each of such independent chromatography systems may comprise two (2) pumps and one (1) column, such that one pump is devoted to loading the column with sample, and one pump for elution.

FIG. 4, reproduced from the aforementioned U.S. Pat. No. 6,635,173, illustrates curves 70, 72, 74, and 76 showing the procedural benefit of controlled staggered/sequenced sample injections as may be performed using the system 50 (FIG. 3). As can be seen, the detector analyzes each curve in sequence. In such regard the detector herein functions to detect and report curve 70, while those samples responsible for curves 72, 74, and 76, although in the process of being eluted in the column, have not yet exited from the column. Such programmed chromatography sequencing is provided herein by a computer control device 63 (FIG. 3) which, upon consideration of when the target sample is likely to exit the column, adjusts the introduction of samples from the autosampler into the columns to sequentially deliver eluant containing sample for sequenced detection. In other words, the computer controller 63 considers the samples in the autosampler, and the input of information concerning their anticipated data-collecting window at the detector, and selects those samples from the autosampler for introduction into the system to maximize detector use.

As indicated in the above discussion, processing of any single sample by a liquid chromatography (LC) system generally begins with an autosampler. Unless otherwise indicated herein, the term "autosampler" is used from this point forward in this document to refer to a modular autosampler, such as the modular autosampler 2 shown in FIG. 2. Unlike operational procedures run by other components, such as pumps and detectors, it is often difficult to determine beforehand the duration of an autosampler procedure. Steps do not necessarily have precise times associated with them. Furthermore, times can vary significantly system to system depending on instrument configuration. In general, such an autosampler executes a programmed procedure of the following general form:

(a) Pre-sample steps (steps executed prior to drawing a sample). This sequence may include wash steps of the syringe and injector, introduction of one or more air gaps (to separate different samples), and movement into position over the position of a sample vial or other sample container. Issues encountered during this phase need not affect sample results. In other words, any malfunctions or other errors encountered during this pre-sample phase will generally not damage or otherwise modify a sample in such a way so as to give incorrect analytical results, since the sample remains in its container. Thus, any such malfunctions or other errors occurring during this phase, if detected by a control system, can possibly be compensated for by simply aborting an existing procedure and re-starting it from the beginning, by switching operations to a backup or concurrently running autosampler or LC system or channel or perhaps, by raising an alarm which will instruct an operator to take corrective action. Spans of time denoting the execution of pre-sample steps are identified by reference symbols including the letter "p" in the accompanying drawings and associated text—for example, a span of time the associated with the execution of pre-sample steps of the $j^{th}$ sample analysis procedure is identified (see FIGS. 5A-5B) with a generalized reference symbol of the form $p_j$. The $k^{th}$ such span of time is identified (see FIGS. 7A-7B) by a generalized reference symbol of the form $p_j(k)$.

(b) Sample Transport. Sample transport begins with physically drawing the sample. This step includes physically moving an aspirated sample and may, optionally, include certain sample preparation steps—such as mixing with a reagent, centrifuging, etc. Any issue encountered during this phase may directly affect the sample being transported. Possible problems which may occur during this phase may include leakage of a sample out of a sample needle (for low-viscosity samples), sample evaporation or time-dependent degradation of the sample, either by exposure of the sample to air, to an unfavorable temperature environment or to ambient light. Accordingly, it is desirable to adjust the timing of commencement of this phase so that the sample is held in the needle or other transport device for no longer than is necessary. Spans of time denoting the execution of sample transport steps are identified by reference symbols including the letter "q" in the accompanying drawings and associated text—for example, a span of time associated with the execution of sample transport steps of the $j^{th}$ sample analysis procedure is identified (see FIGS. 5A-5B) with a generalized reference symbol of the form $q_j$. The $k^{th}$ such span of time is identified (see FIGS. 7A-7B) by a generalized reference symbol of the form $q_j(k)$.

(c) System Synchronization ("Sync"). The autosampler may wait for confirmation that an LC system is ready to receive an injection. The sync may operate through either software or hardware mechanisms. Because some samples may be reactive or prone to degradation or loss as noted above, it is desirable to minimize such waiting time. These "Ready" signals are identified by reference symbols 81a-81d in FIGS. 5A-5B and reference symbols 85a-85c in FIG. 7A.

(d) Injection. The system injects the sample into the LC system and starts other LC devices, effectively transferring control of the sample. Each injection operation requires a brief but finite time period—these are represented by time periods noted as $t_{inject}$ in FIGS. 5A-5B. The completion of injection is indicated by reference symbols 83a-83d in FIGS. 5A-5B and reference symbols 87a-87b in FIG. 7A. At such times, injection-completed signals may be transmitted from the autosampler the LC channel system.

(e) Post-Injection Operations. The autosampler may execute several other operations on the back end of the program. Spans of time denoting the execution of post-injection steps are identified by reference symbols including the letter "z" in the accompanying drawings and associated text—for example, a span of time associated with the execution of post-injection steps associated with the $j^{th}$ sample analysis procedure is identified (see FIGS. 5A-5B) with a generalized reference symbol of the form $z_j$. The $k^{th}$ such span of time is identified (see FIGS. 7A-7B) by a generalized reference symbol of the form $z_j(k)$.

Full time spans including some or all of the austosampler procedural steps (a)-(e) above are identified by reference symbols including the letter "r" in the accompanying drawings and associated text—for example, time spans $r_1$, $r_2$, $r_3$ and $r_4$ in FIGS. 5A-5B. FIG. 5A illustrates a first example of a conventional timing scheme for coordinating the operation of an autosampler and an LC system. The horizontal axis in FIG. 5A represents time. In FIG. 5A, as well as in FIG. 5B and FIG. 7, boxes at the base of the diagram represent periods of time during which a liquid chromatography channel—such as a liquid chromatography/mass spectrometry (LC/MS) system or a single channel thereof—is busy performing the operations of separating components of and possibly identifying or quantifying chemical species within a previously injected sample. Different patterns applied to boxes at the base of the diagram represent either different samples or different sample analysis procedures, denoted as $s_i$ (where i is an integer) such as samples or procedures $s_1$, $s_2$ and $s_3$. Boxes drawn in solid lines at the top of the diagrams of FIG. 5 and FIG. 7—specifically, boxes $r_1$, $r_2$, $r_3$ and $r_4$—represent periods of time that a robotic autosampler devotes to performing steps (a)-(e) as listed above; un-patterned boxes drawn in dotted lines represents auto-sampler idle time, either as the result of an intentional delay period or else during which the autosampler is waiting for the LC channel or system to become available.

To improve timing between subsequent samples, a typical strategy, as illustrated in FIG. 5A, has been to start the autosampler as early as possible on subsequent samples. Thus, as may be seen in FIG. 5A, autosampler operational procedure $r_2$, relating to preparation for injection of a sample whose analysis is noted at $s_2$, commences immediately after injection of a prior sample whose analysis is noted at $s_1$. Since the robot operations may require a time period of 1-3 minutes whereas the sample analyses may require substantially longer periods—for instance 4-12 minutes, this so called "Look-Ahead" methodology, may frequently lead to situations in which an autosampler has completed steps prior to injection and thus spends a significant period of time waiting for the "System Sync" to continue. Such waiting periods are denoted by the time intervals $\Delta t_{r1}$, $\Delta t_{r2}$ and $\Delta t_{r3}$ in FIG. 5A. The existence of such waiting periods can have several negative consequences: (i) samples sensitive to temperature or other factors may be affected by the length of time spent in the syringe and also by the potential time variations seen between samples; (ii) samples with very low viscosity may begin to drip or mix across air gaps; and (iii) the probability of losing a sample due to an abort or error of a previous sample is increased.

A second a conventional timing scheme for coordinating the operation of an autosampler and an LC system is illustrated in FIG. 5B. The procedure illustrated in FIG. 5B attempts to overcome the above-noted fact that it is preferable to minimize the time a sample spends in the dispensing syringe or needle by attempting to start the auto-sampler such that it is ready to make an injection—that is, the "pre-injection" steps (a) and (b) are completed—just prior to receipt of a "System Sync" signal. This method utilizes a timing-data database 206 that contains autosampler timing estimates entered manually by users based on record-keeping of the time required to conduct autosampler operations during previous analytical runs. Since the various autosampler operation times may vary between different samples or different sample analysis procedures, such as samples or procedures $s_1$, $s_2$ and $s_3$, different timing estimates should be maintained, in parallel, for each of the various samples or procedures. Also the times required to undertake the various LC sample analyses are expected to vary between the different samples or procedures $s_1$, $s_2$ and $s_3$, etc., as is indicated by the varying widths of the differently patterned boxes along the time axis.

The time estimates in the database 206 (FIG. 5B) are used to calculate predetermined autosampler "lag times" that measure the time between the injection of a sample into the LC system and prior to the commencement of the sequence of autosampler steps associated with the next sample. Thus, for instance, in FIG. 5B, the quantity $\Delta t_{r2}^{s1}$ represents the predetermined autosampler lag time that measures the time interval from the commencement of execution of the LC sample or procedure $s_1$ until the beginning of the sequence of autosampler steps, $r_2$, required to execute pre-sample steps (a) and sample transport steps (b) in preparation for injecting the sample associated with the next analysis indicated at $s_2$. Each "lag time", so defined, is related but to not necessarily identical to a "delay time" which is a wait time inserted between the completion of autosampler post-injection steps and the commencement of the sequence of autosampler steps associated with the next sample. Such delay times, so defined, are indicated by the time segments outlined in dotted lines in FIG. 5B. As indicated in FIG. 5B, the correct calculation of the predetermined delay time or, equivalently, lag time, will cause the autosampler to finish its pre-injection steps (indicated by the shaded boxes $p_2$ and $q_2$) just about at the same time that the LC system transmits the System Sync signal 81b indicating that it is ready to receive the sample associated with the analysis indicated at $s_2$.

Similarly, the quantity $\Delta t_{r3}^{s2}$ (FIG. 5B) represents another predetermined autosampler lag time. This lag time measures the time from the commencement of execution of the LC sample or procedure $s_2$ until the commencement of the sequence of autosampler steps, $r_3$, required to prepare to inject the sample associated with the next analysis indicated at $s_3$. In this hypothetical case, FIG. 5B indicates that the lag time and associated delay time (dotted line time segment after post-injection steps $z_2$), as calculated from the user-estimated data, was too short, causing the existence of an un-planned autosampler idle time while the autosampler module waits for receipt of the System Sync signal 81c. The next predetermined autosampler lag time, $\Delta t_{r4}^{s3}$ (which in this instance is equivalent to the delay time) is inserted immediately after the commencement of execution of the LC sample or procedure $s_3$ and prior to beginning the sequence of autosampler steps, $r_4$, required to prepare to inject the sample associated with the next analysis indicated at $s_4$. In this particular hypothetical case, FIG. 5B indicates that the lag time, as calculated from the user-estimated data, was too long, thereby causing LC system to idly wait for a period time while the autosampler completes its pre-injection steps after the LC system signaled, at 81d, that it was ready to receive the sample. Such delays in the operation of the LC system can lead to overall analytical inefficiency which can become significant during the running of numerous samples of a batch.

The procedure illustrated in FIG. 5B requires diligence and conscientiousness by users to enter timing settings and to adjust them whenever necessary. Such timing setting adjustments should generally be entered whenever an LC analytical procedure or an autosampler procedure is modified. Typically, these procedures may both be modified in concert. Timing adjustments should also be entered whenever an analytical procedure is transferred to another system, since the timings are generally machine-specific. Failure to make such adjustments can seriously affect multiplexing timing efficiency and, as noted above, can effect overall system efficiency or can cause degradation or loss of samples. Moreover, robotic sample aspiration, transport and dispensing operations and multiplexed chromatography systems (FIGS. 1-3) are typically associated with systems designed for automated screening operations, such as high-throughput screening (HTS) systems involving virtually continuous sequences of analyses and large numbers of samples. Such automated high-throughput systems are often utilized, for instance, in drug-discovery procedures and may be used for clinical applications such as drug-testing or screening for vitamin deficiencies or for diagnostic biomarkers. Such automated screening systems are frequently designed for unattended or overnight operation with little operator intervention other than initial loading of samples. In such systems, sample containers may be accessed in a "random" fashion which is generally unpredictable to a user—as may be the case of the sample access and analysis operations are under the control of a computerized scheduler, as may occur with multiplexed chromatographic systems. Because of these factors, it may be difficult or impossible, in practice, for a user to manually maintain detailed logs of elapsed autosampler times for different sample types or procedures.

SUMMARY OF THE INVENTION

In accordance with the present teachings, software automatically tracks various timing characteristics of each analytical procedure in use in an LC system coupled to a modular autosampler. The software uses these timing characteristics in a predictive model to start an autosampler at the optimum time; such that little to no time is spent waiting for system synchronizations. As samples are run, software continually tracks "Pre-Sample" and "Pre-Injection" times for each sample. The software maintains a record of the longest times encountered for each parameter of each method in use. Time spent waiting for synchronization signals is not considered when generating these timing records. Also, if a deviation is encountered (such as a hold, error, or abort event) during analysis of a particular sample, all or part of the method timing parameters relating to that sample are discarded. Using timing data obtained from recently performed chromatography experiments, the most current values of longest time delays are used to predict when the autosampler should begin executing its programmed sequence of operations. Generally, this will occur when the time remaining on a previous sample run is equivalent to the total Pre-Injection time for a pending auto-sampler procedure. With multiplexing, the predictive methods taught herein can additionally use the Pre-Sample time to best optimize "Detector Reset" delay times.

The present invention provides several important Benefits. In a single channel system, variations in the time that a particular sample may be held are minimized and, consequently, the risk associated with holding the temperature of or otherwise excessively handling a sensitive sample is minimized. Additionally, the risk of losing or damaging a sample being transported by the autosampler due to an error or abort elsewhere in an autosampler system is minimized. In a multiplexed system, method embodiments according to the present invention are able to automatically optimize multiplexing efficiency while maintaining maximum flexibility and robustness.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To appreciate the features of the present invention in greater detail, please refer to FIGS. 1-8 in conjunction with the following discussion.

Figure 1A:
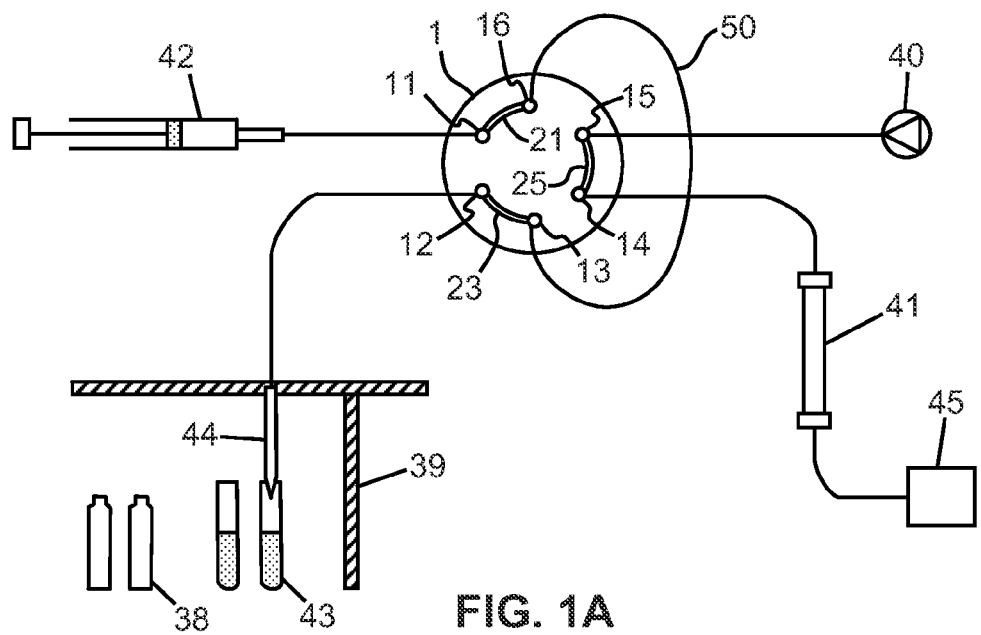
FIG. 1A is a simplified schematic representation of an autosampler according to prior art with a high-pressure injection valve and with connected fluidic components, wherein the valve is in the LOAD position.
Figure 1B:
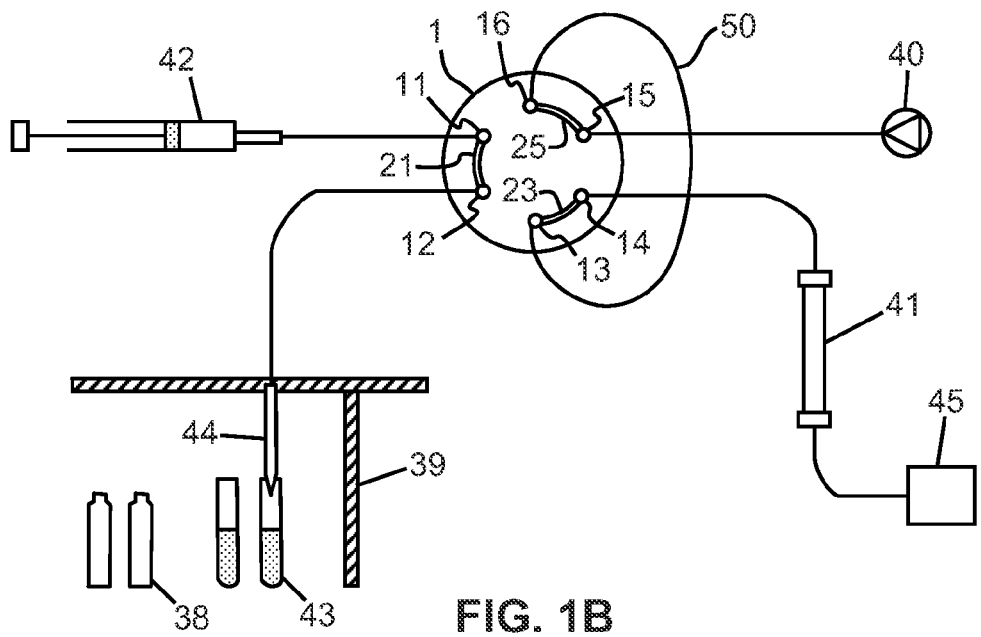
FIG. 1B is a representation analogous to FIG. 4, but with the high-pressure valve in the INJECT position.
Figure 2:
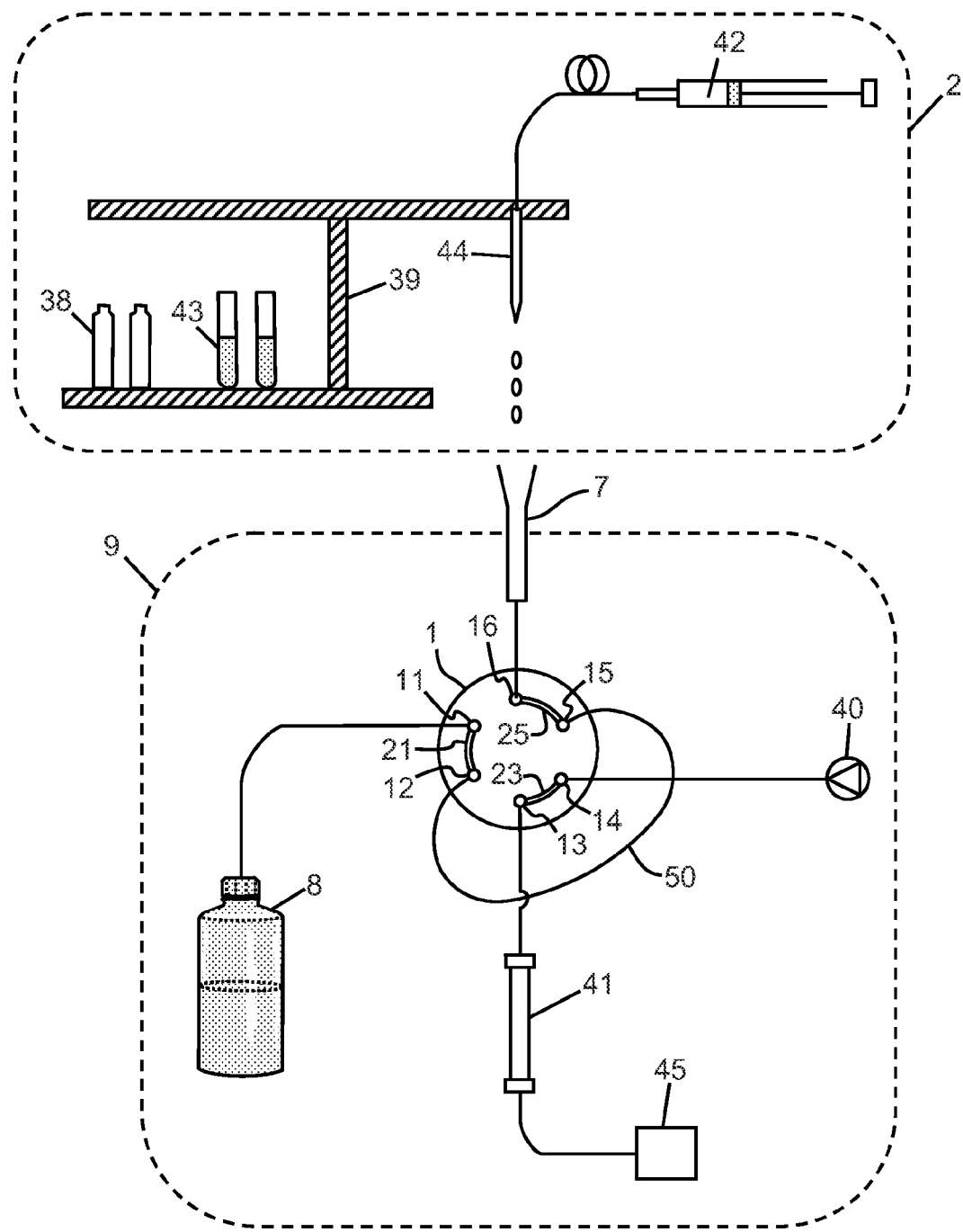
FIG. 2 is a simplified schematic representation of a modular robotic autosampler system coupled to a modular liquid chromatography (LC) system.
Figure 6:
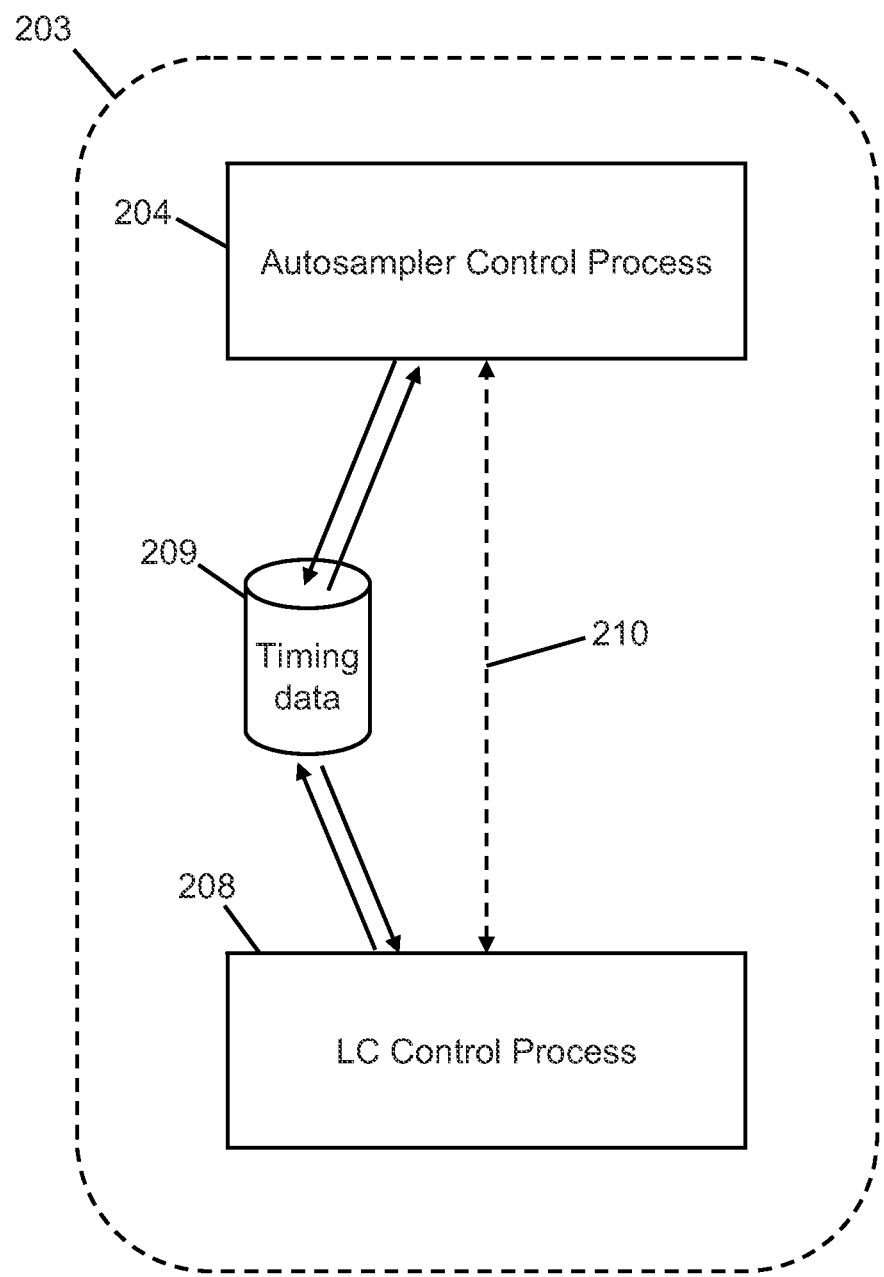
FIG. 6 is a schematic illustration of a preferred control software architecture for implementing methods in accordance with the present teachings.

FIG. 6 is a schematic illustration of a preferred control software architecture for implementing methods in accordance with the present teachings. The modular software architecture system 203 illustrated in FIG. 6 is useful for— but not limited to—control of the operation of a system comprising the modular hardware architecture shown in FIG. 2, with a modular autosampler fluidically and electronically coupled to a modular LC system, such as an LC/MS system. In this discussion, it is to be kept in mind that the hardware components illustrated in FIG. 2 are illustrated in schematic and simplified form and that any real system may comprise various additional components. The novel methods disclosed herein are intended to be applied generally to any system comprising coupled autosampler and LC modules. The modular software architecture illustrated in FIG. 6 is implemented within a computer system or other controller system that is electronically coupled to both the autosampler module and to the LC module (but which is not specifically illustrated in FIG. 2).

The modular software architecture system 203 (FIG. 6) comprises an autosampler control process and an LC control process. Each of the autosampler control process and the LC control process may be implemented in its own separate module—i.e., an autosampler control process module 204 and a separate LC control process module 208—each module containing code specific for executing its respective process. In the following discussion, references to each of these process modules can be replaced with references to just the respective process, without any loss of generality. The autosampler control process module 204 and LC control process module 208 function concurrently and mostly independently of one another but may pass timing synchronization signals and other information between them. Updated instrument timing data is maintained within a computer-readable memory module 209, such as a hard disk drive, flash memory or any other form of data storage. Either the autosampler control process module 204 or the LC control process module 208 may store timing data, other status data or other information on the readable memory module 209 so as to be subsequently read by the other of the modules. Low-level timing or synchronization signals may be passed between the modules by means of a data line 210.

The autosampler control process module 204 may comprise instructions to mechanically control the horizontal and vertical location of an aspirating and dispensing needle or syringe, to control the position of a moveable tray or carousel that holds various sample containers temporarily housed in or on the autosampler, to control one or more valves which direct various fluids—as, for instance, washing solutions—through the syringe or needle, to control one or more pumps that are used to draw fluid into or dispense fluid out of the needle or syringe, to control the physical environment—for instance, temperature—of various fluid or sample reservoirs on or in the autosampler, among various other functions. The autosampler control process module 204 also comprises a timer capability to keep track of the time required for various autosampler operations and may also comprise instructions to read various sensors of the autosampler, such as position sensors, temperature sensors, fluid level sensors, etc.

The LC control process module 208 may comprise instructions to, to control one or more valves which direct various fluids—as, for instance, buffer solutions, washing solutions, various mobile phases—through one or more columns of an LC instrument or to waste, to control one or more pumps that urge fluids into and through the various columns, sample loops and other tubing interconnections of the LC system, to control the physical environment—for instance, temperature—of various fluid reservoirs, sample reservoirs or columns of the LC system, among various other functions. The LC control process module 208 may further comprise instructions to control various operating parameters of a detector that receives separated chemical species from the LC system and to read information relating to the species from the detector.

Figure 5A:
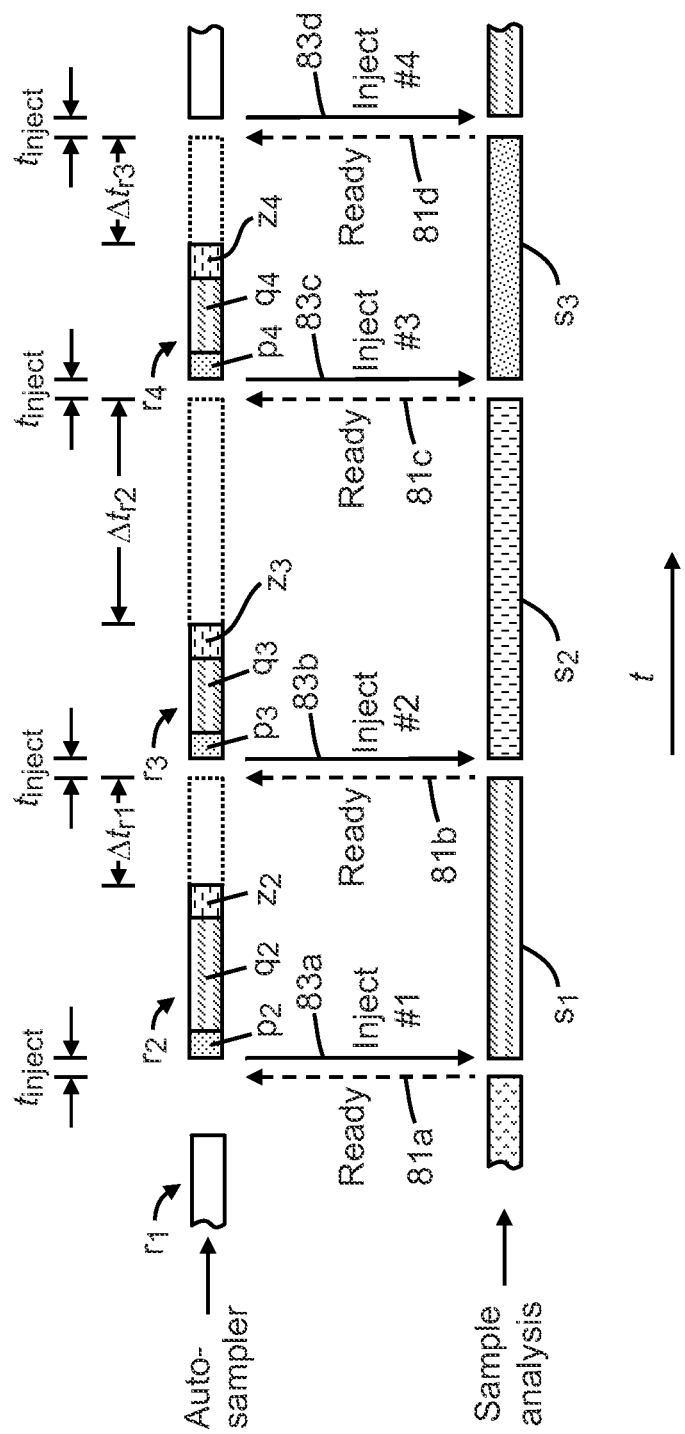
FIG. 5A is a schematic illustration of a first conventional method for coordinating the operation of an autosampler and an LC system.
Figure 5B:
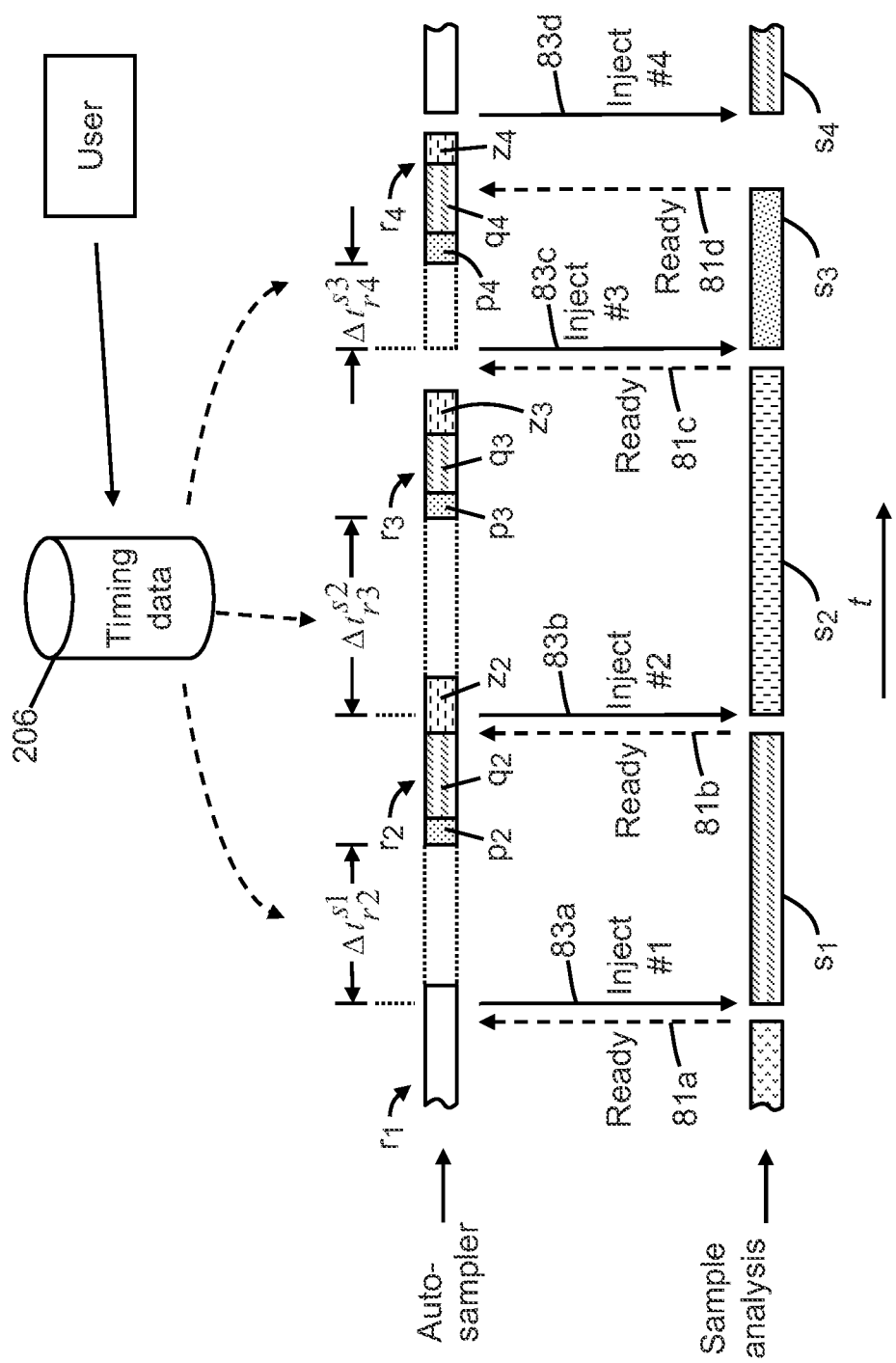
FIG. 5B is a schematic illustration of a second conventional method for coordinating the operation of an autosampler and an LC system.
Figure 7A:
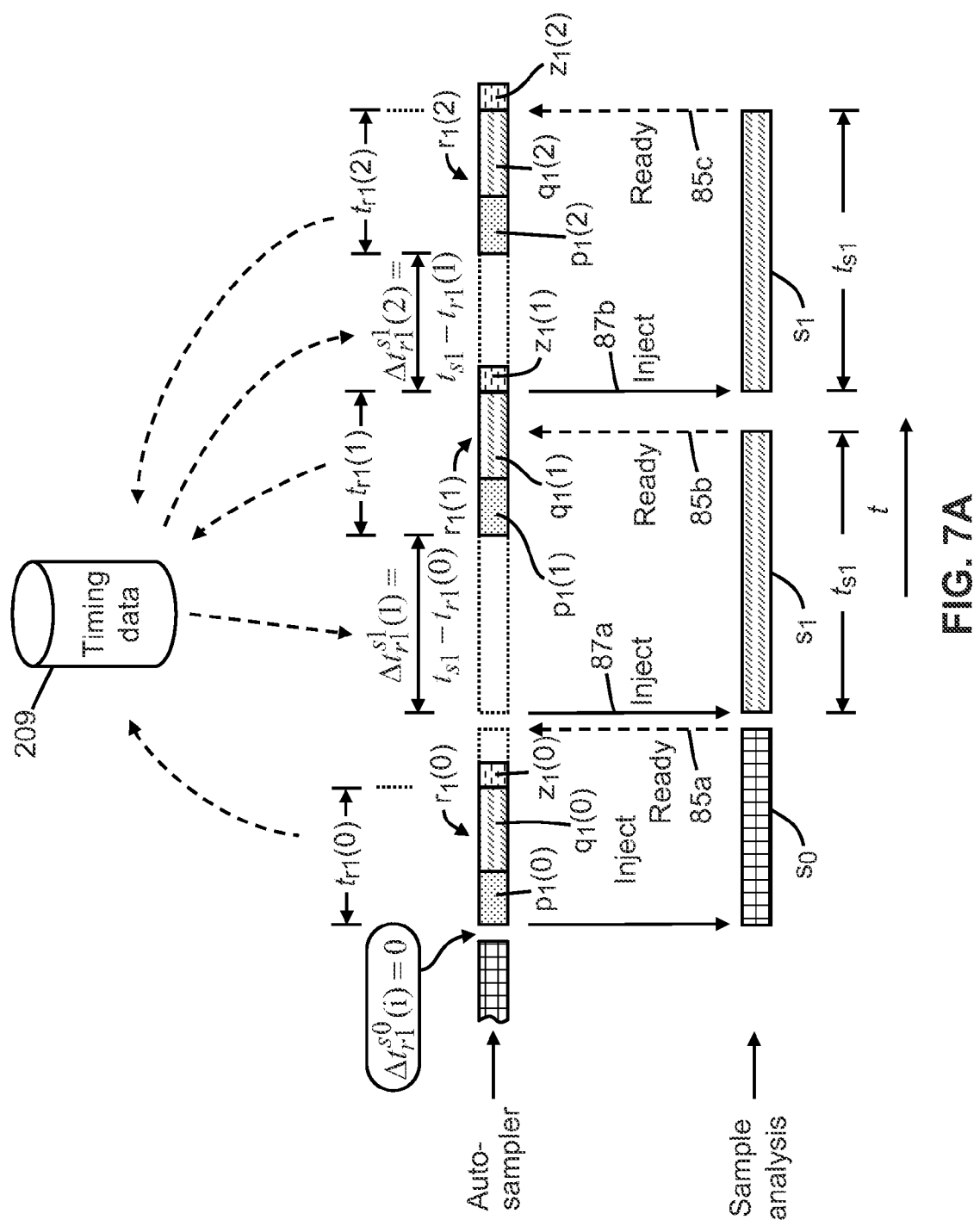
FIG. 7A is a schematic illustration of a method for optimizing the operation of an autosampler and an LC system in accordance with the present teachings.

FIG. 7A is a schematic illustration of a method for coordinating the operation of an autosampler and an LC system in accordance with the present teachings, using a similar format to that provided in FIGS. 5A-5B, with time, t, progressing from left to right across the diagram. The illustration in FIG.

7A only considers the controlling of and the updating of records of timing data relating to one particular chromatographic sample analysis procedure, denoted as $s_1$. For instance, the procedures $s_1$ could comprise a particular assay, a particular assay applied to a particular class of samples or to a particular sample, etc. For purposes of illustration, the various instances of execution of the procedure $s_1$ are indicated as occurring consecutively. Although such repetitive execution of a single analytical procedure may occur in many instances, different analytical procedures may be interspersed with one another in various other situations, perhaps in order of priority, in some other pre-determined order or, possibly, in random fashion.

Because the conditions under which chromatography experiments are run are performed under tight constraints designed to maintain the experiments of constant duration, the sample analysis time, which is the time required to perform the particular LC analysis procedure is assumed, for purposes of this initial discussion, to be maintained at the constant value of $t_{s1}$. This quantity is the time between which sample injection is complete and the subsequent indication, by the LC system, that it is ready to receive another sample. If the quantity $t_{s1}$ cannot be assumed to be constant, then the variation of this quantity may be noted by the LC control process module 208 and recorded in the timing database (in addition to the autosampler times) so as to be incorporated into the calculations of autosampler delay times. Further, because each LC analysis procedure (e.g., procedures $s_1$, $s_2$, $s_3$, etc., see FIG. 5) may be associated with its own unique, different time (e.g., $t_{s1}$, $t_{s2}$, $t_{s3}$, etc.) required to perform the respective procedure, the procedure for calculation of autosampler delay times may take into account not only the time required to perform the autosampler operations associated with preparing to inject the next sample but, also, the time required to perform the procedure that that is executed just prior to injection of the next sample into a liquid chromatograph. Accordingly, the $k^{th}$ instance of the lag time implemented prior to the pre-injection autosampler functions preparatory for analysis procedure $s_i$ at a time that procedure $s_j$ is executing is herein denoted by the symbolism $\Delta t_{ri}^{sj}(k)$.

Returning to the discussion of FIG. 7A, a first injection in preparation for a first execution (index k=1) of the $s_1$ analytical procedure begins after a System Sync signal 85a indicating that the LC system is ready to receive a sample, after finishing a prior analytical procedure, $s_0$. The various instances of execution of the autosampler pre-injection operations prior to running the $s_1$ procedure are indicated by segmented boxes drawn in solid lines and are indicated, in sequence, by the symbols $r_1(0)$, $r_1(1)$ and $r_1(2)$. For the initial injection, it may happen that no prior timing data will be available in the timing database. Accordingly, in this example, $\Delta t_{r1}^{s0}(i)=0$—that is, no time delay is implemented prior to the first execution of the autosampler operations $r_1(0)$, which occur while the prior procedure $s_0$ is being executed. Other situations in which the delay time may be set to zero may occur if the database has been corrupted, if the procedure has been modified or if the procedure has been ported to a new instrument.

In the hypothetical example illustrated in FIG. 7A, the time duration of autosampler pre-injection operations (comprising pre-sample operations $p_1(0)$ and sample transport operations $q_1(0)$ of the autosampler) during the procedure $r_1(0)$ is measured to be $t_{r1}(0)$. In general, the autosampler control process module maintains a record of the maximum previously encountered value of the time required for the autosampler pre-injection operations, denoted, in this instance as $t_{r1}^{max}$, which is given as $t_{r1}^{max}=\max\{t_{r1}(0), t_{r1}(1), t_{r1}(2), \ldots, t_{r1}(n)\}$.

In a practical sense, the autosampler control process module compares the most recently encountered value with the maximum value already in the database and, if the newly-measured value is greater than the prior maximum, simply replaces the old maximum value with the newly measured value. After the first execution of the autosampler pre-injection operations associated with the analytical procedure $s_1$, the first time value, $t_{r1}(0)$, is the maximum value and, accordingly, this value is recorded.

When the LC system module provides the "Ready" signal 85a, the sample to be analyzed by the analytical procedure $s_1$ is injected at 87a and the procedure $s_1$ is initiated. The next instance of execution of autosampler pre-injection operations $r_1(1)$ does not begin immediately, but instead occurs after a time delay corresponding to or determined from the lag time $\Delta t_{r1}^{s1}(1)$ which is calculated, generally as $\Delta t_{r1}^{s1}(1)=t_{s1}-t_{r1}^{max}$, where the value of $t_{r1}^{max}$ is retrieved from the timing database. Using the maximum of all previously encountered pre-injection times ensures that the autosampler module will almost always commence operations early enough so as to complete its pre-injection tasks prior to the time at which the LC module is ready to receive a sample, thereby ensuring that the system operates efficiently. In this particular instance, the inserted time delay (the delay time) is simply the lag time $\Delta t_{r1}^{s1}(1)=t_{s1}-t_{r1}(0)$.

In this hypothetical example, the time duration required to execute the autosampler pre-injection operations is not constant and, the time duration, $t_{r1}(1)$, of autosampler pre-injection operations of the procedure $r_1(1)$ is greater than the time duration, $t_{r1}(0)$, of the initial execution of this operational sequence. As a result, the execution of autosampler pre-injection operations $p_1(1)$ and $q_1(1)$ is seen to extend beyond the time—at System Sync signal 85b—at which the LC system is ready to receive a sample, thereby causing the LC system to wait until the injection is subsequently completed, later than expected, at 87b. Because, in this case, $t_{r1}(1)>t_{r1}^{max}=t_{r1}(0)$, the newly encountered time duration $t_{r1}(1)$ becomes the new maximum value recorded in the database. The subsequent autosampler lag time, $\Delta t_{r1}^{s1}(2)$, is calculated using this new value of $t_{r1}^{max}$. In this hypothetical example, this subsequent lag time and its corresponding time delay are correctly calculated such that the next autosampler pre-injection operation sequence comprising operations $p_1(2)$ and $q_1(2)$, terminates at the expected time, when the LC system provides the next System Sync signal 85c.

Figure 7B:
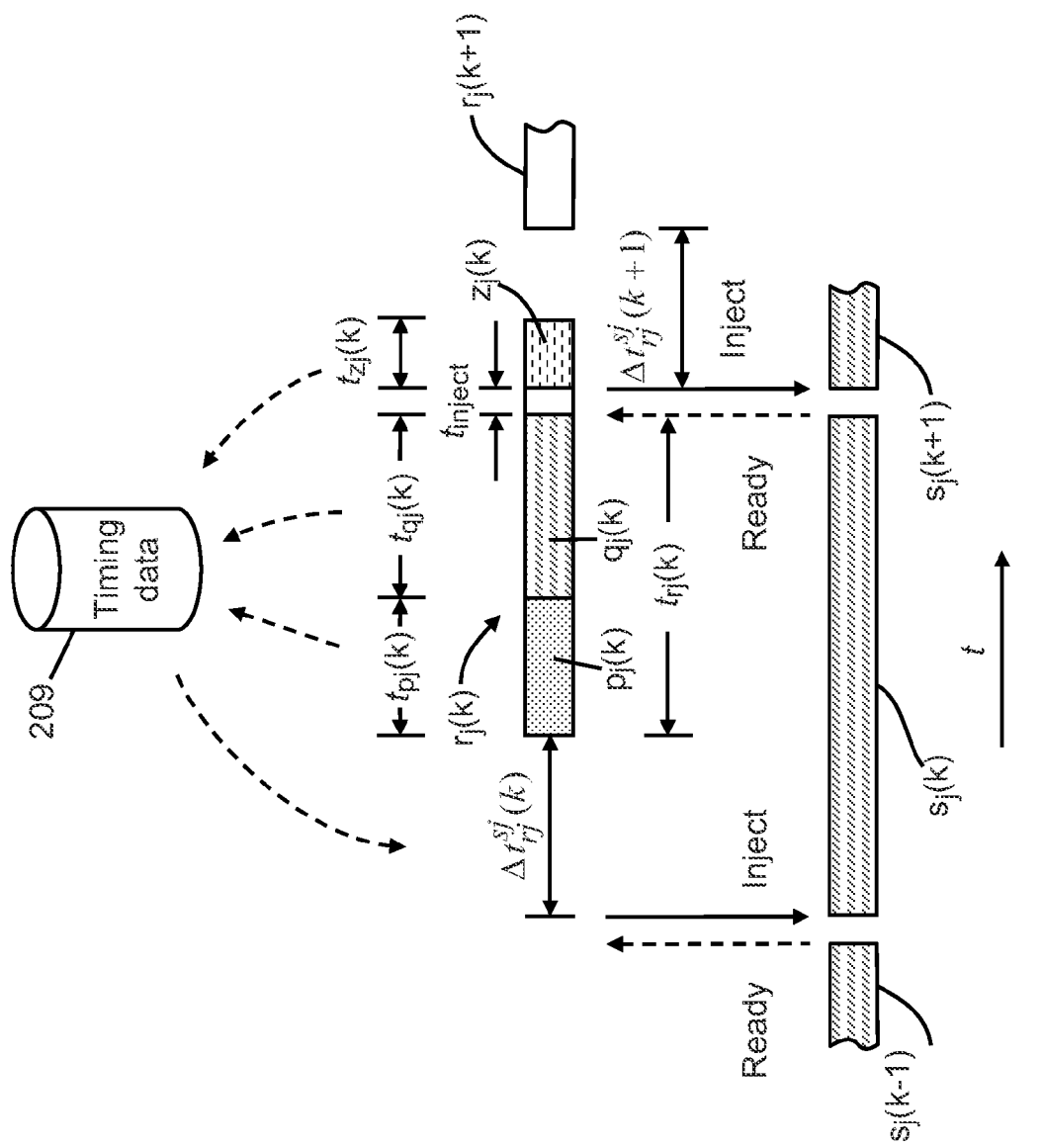
FIG. 7B is a schematic illustration of a variation to a method for optimizing the operation of an autosampler and an LC system in accordance with the present teachings.

As discussed previously, the pre-injection steps referred to in the above discussions comprise initial pre-sample steps (a) followed by subsequent sample transport steps (b). Accordingly, the pre-injection time may be decomposed into: (a) a pre-sample time during which all preparatory steps prior to withdrawing a sample from a sample container are executed and (b) a sample transport time during which the aspirated sample in a needle or syringe is moved from to an injection port. FIG. 7B illustrates in detail the events in the vicinity of the $k^{th}$ execution of the LC analytical procedure $s_j(k)$ and the concurrent autosampler procedure $r_j(k)$ having a pre-injection time duration of $t_{rj}(k)$. As may be seen in FIG. 7B, this time duration is comprised of a pre-sample time component, $t_{pj}(k)$ and a sample transport time component $t_{qj}(k)$, such that $t_{rj}(k)=t_{pj}(k)+t_{qj}(k)$. As discussed previously, the autosampler procedure $r_j(k)$ will generally comprise an additional time components $t_{inject}$, which is the time required to dispense the sample and $t_{zj}(k)$, which is the time associated with post-injection operations $z_j(k)$.

The previous discussion has noted that the maximum encountered value of the total pre-injection time may be stored in a database and used to calculate autosampler lag times and their corresponding delay times. It may only be necessary to store time values relating to the total pre-injection time, provided that autosampler lag times are measured from the time of completion of sample injection into the LC system. However, it is nonetheless also possible to maintain separate records of the component values $t_{pj}(k)$ and $t_{qj}(k)$ and, possibly, $t_{inject}$, or $t_{zj}(k)$. The timing database may maintain records of the actual time intervals or, alternatively, of one or more quantities derived from the time values, such as a maximum value, minimum value, average value or standard deviation of values. The records relating to the pre-sample time component, $t_{pj}(k)$ and the sample transport time component $t_{qj}(k)$ may be useful if a system error occurs during processing of a sample, since the best error recovery procedure may depend on whether the autosampler was performing pre-sample operations or transport operations at the time of the error. In case of an error, the elapsed time since the most recent "Ready" System Sync signal may be compared to the time values in the database and used to determine the processing stage of the autosampler at the time of the malfunction. For instance, if a malfunction occurs in a detector component of an LC system while the autosampler is performing pre-sample operations, then the autosampler control process module may simply abort the currently executing steps and re-start operations when the detector is once-again functional since, in this case, the sample on which an analysis was to be performed remains undisturbed in its original container. However, if the same error occurs during the sample transport stage, then the sample may need to be discarded, since the integrity of the sample and the accuracy of analytical results obtained from it are generally at risk once a portion of sample has been withdrawn. In a multiplexing system that includes a single autosampler that can perform an injection into any one of multiple LC channels via a respective injection valve (e.g., see FIG. 3), then if a malfunction occurs in a channel that was to be the destination of a sample already in transport in the autosampler, the autosampler may be directed to wait for next availability of one of the still-functioning LC channels and to re-direct the sample injection to that channel.

Figure 8A:
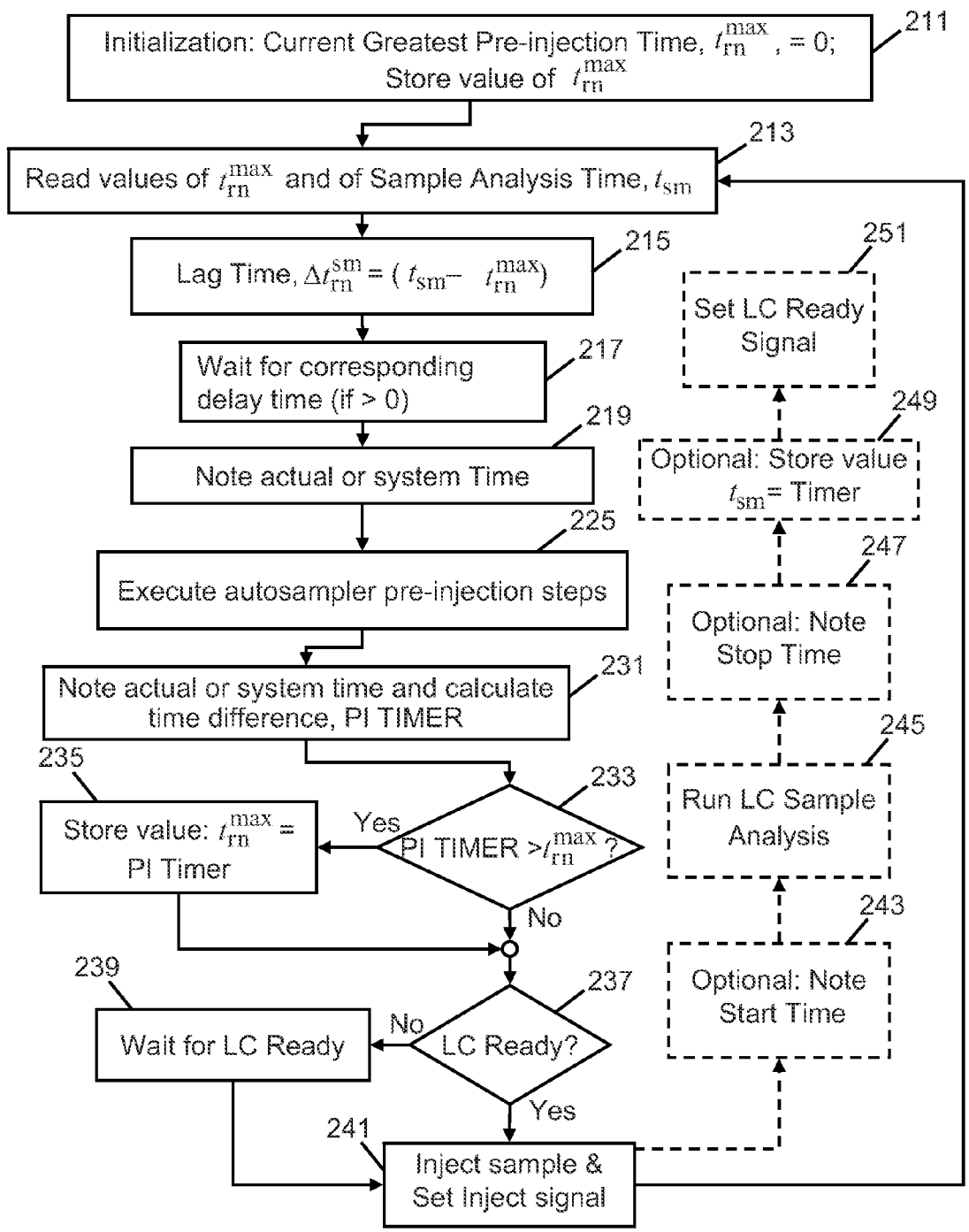
FIG. 8A is a flow diagram for a method for optimizing the operation of an autosampler and an LC system in accordance with the present teachings.

In accordance with the discussion above, FIG. 8A is a flow diagram of a first method, method 210, in accordance with the present teachings, for optimizing the operation of an autosampler and an LC system. The first step, Step 211, is an initialization step in which the Current Greatest Pre-injection Time for the $n^{th}$ analytical procedure, in other words, the maximum previously encountered value of the time required for the autosampler pre-injection operations, $t_{rn}^{max}$, is set to zero and stored in the timing database. The $n^{th}$ analytical procedure is the next analytical procedure (in a sequence of analytical procedures) to be run by the system. The index "n" (where $1 \leq n \leq N$) is provided to identify a particular type of analytical procedure or procedural format—for instance, a type of sample analysis such as a particular type of assay—out of a total of N possible types of analytical procedures or procedural formats which may be executed by the system. It is possible that N=1 in which case the system always executes one type of analytical procedure.

Subsequent steps 213-241 comprise a main iterated loop of the method 210 (FIG. 8A). In Step 213, timing data is input or read from the timing database. This data that is input will at least include the most recent value of $t_{rn}^{max}$. Of course, a different value of $t_{rn}^{max}$ will generally be stored in the database for each value of the index n (where $1 \leq n \leq N$). The input data may also possibly include the value of the required sample analysis time, $t_{sm}$, for the currently executing LC analytical procedure, generally the $m^{th}$ analytical procedure and the starting time $t_{start}$ of that procedure. The currently executing analytical procedure (the $m^{th}$ procedure) may or may not be the same analytical procedure as the procedure (the $n^{th}$ procedure) for which the autosampler is conducting preparatory steps. The quantity $t_{sm}$ may be a constant, or alternatively, it may comprise a measured value obtained from previous execution of the $m^{th}$ procedure by the system or may comprise a derived quantity such as a minimum observed value, maximum observed value, average value, etc. The quantities $t_{rn}^{max}$ and $t_{sm}$ are used, in the next step, Step 215, to set an autosampler lag time, $\Delta t_{rn}$, which is calculated as $\Delta t_{rn}^{sm} = (t_{sm} - t_{rn}^{max})$. In the next step, Step 217, the autosampler waits for a period of time corresponding to the calculated autosampler delay time, if the calculated autosampler delay time is greater than zero. The delay time, $\Delta t_d$, that corresponds to the lag time may be calculated from $\Delta t_d = (t_{start} \Delta t_{rn}^{sm}) - t$ in which $t_{start}$ is the clock time (actual or system time) that was recorded (e.g., in Step 243) when the currently executing LC analysis procedure started and t is the current clock time.

The autosampler commences its pre-injection sequence of operations in Step 225 of the method 210 (FIG. 8A). However, prior to doing so, the time at the commencement of the autosampler operations—for instance, a system time—is noted in Step 219 in order to keep track of the subsequent time required to perform the pre-injection operations. Alternatively, a timer (pre-injection timer or PI Timer) may be started in Step 219 such that the timer might operate as a stopwatch. In Step 231, after execution of the autosampler pre-injection steps, note is made of the actual time at the completion of the autosampler steps and a time difference is calculated. Alternatively, the dedicated timer, if utilized, is stopped. The program variable PI TIMER (or some other name) stores this time difference or Timer value. In Step 233, the value of PI TIMER is compared to the maximum previously encountered value of the time required for the autosampler pre-injection operations, $t_{rn}^{max}$. If the value of PI TIMER is the greater quantity, then $t_{rn}^{max}$ is reset to the value of PI TIMER, which new value is stored in the database, in Step 235.

In Step 237 of the method 210 (FIG. 8A), a check is made to determine if the LC system is ready to receive the aspirated sample from the autosampler (e.g., if an LC ready System Sync signal has been transmitted or set). If not, the autosampler waits, in Step 239, for the receipt of such a signal. Once the LC system is ready, then, in Step 241, the sample is injected into the LC system and a signal (e.g., an Inject signal) may be transmitted or set so as to notify the LC system to begin the sample analysis operations.

The steps outlined in solid-line boxes in FIG. 8A may generally be carried out by an autosampler control process (e.g., process 204 in FIG. 6) in a multiprocessing system that also includes an LC control process (e.g., process 208 in FIG. 6). Accordingly, after step 241 of the method 210 is executed, the in-process flow loops back to Step 213. However, several steps from a concurrently executing LC control process are shown in boxes with dotted lines in FIG. 8A, since these steps are triggered by the sample injection and transmission or setting of an Inject signal in Step 241. Thus, in Step 245 of the method 210, the LC control process executes all of the various steps involved in performing the analysis of the recently injected sample. Prior to doing so, however, note is optionally made of the actual or system time (or a timer is started) so as to keep track of the total time required, $t_{sn}$, to perform the $n^{th}$ sample analysis procedure. This time is the total time between receipt of an Inject signal by the LC system and the transmission of a next LC Ready signal by the system. In Step 247, note is made of the actual or system time at the end of the LC analysis procedure and a time difference is calculated. Alternatively, the dedicated timer, if utilized, is stopped.

It may be useful to maintain, within the timing database, a record of the sample analysis time for the $m^{th}$ procedure, $t_{sm}$, corresponding to each execution of the analysis procedure. Alternatively, a record may be retained only for a derived quantity, such as, for instance, an average of several measurements of $t_{sm}$ or a greatest encountered value or a minimum encountered value of $t_{sm}$. Of course, a different value of $t_{sm}$ will generally be stored for each value of the index m (where $1 \leq m \leq N$). Such records may be useful because, as indicated in FIG. 7A, the autosampler delay time calculation takes this quantity into account. Although chromatography experiments are generally performed under tight constraints designed to maintain the experiments of constant duration, it is possible that the sample analysis time may vary over the course of several LC procedures. If this happens, a database record of such variation can enable continuous calculations of optimal delay times. The current value of $t_{sm}$ or of a quantity derived therefrom is thus optionally stored in the database in Step 249 of the method 210. If it is desired to ensure that the autosampler module will almost always commence operations early enough so as to complete its pre-injection tasks prior to the time at which the LC module is ready to receive a sample, then it may be desirable, in this step, to compare the most recent value of $t_{sm}$ to a minimum observed value of this quantity and to replace the previous minimum with the most recent value of $t_{sm}$ if this value is less than the previous minimum.

Figure 8B:
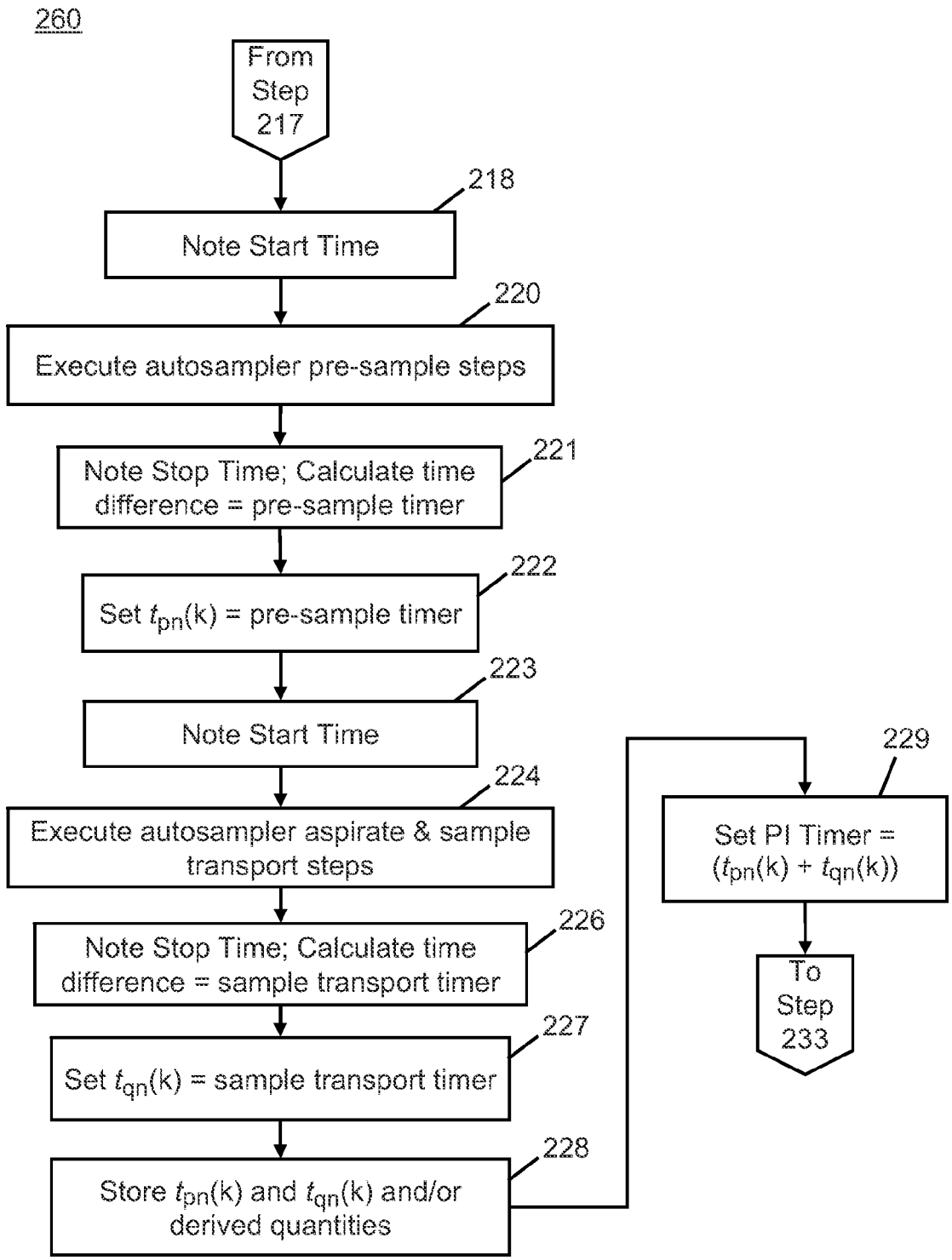
FIG. 8B is a flow diagram of a portion of an alternative method for optimizing the operation of an autosampler and an LC system in accordance with the present teachings.

FIG. 8B is a flow diagram illustrating a portion of an alternative method, method 260, in accordance with the present teachings. Steps 211-217 and Steps 233-251 of the method 260 (FIG. 8B) are identical to the corresponding steps of the method 210 (FIG. 8A) and, therefore, these steps are not reproduced in FIG. 8B. The illustrated steps 218-229 of the method 260 replace the Steps 219, 225 and 231 previously shown in FIG. 8A. The method 260 differs from the method 210 through the provision (in method 260) of keeping separate records of the pre-sample time, $t_{pn}$, and the sample transport time, $t_{qn}$, relating to the $n^{th}$ sample analysis procedure. The quantities $t_{pn}(k)$ and $t_{qn}(k)$ shown in FIG. 8B are the values of pre-sample time and sample transport time observed for the $k^{th}$ execution of the $n^{th}$ procedure. It is possible to store records comprising a plurality of measurements these quantities or else to store derived quantities, such as an average, a maximum observed value, a minimum observed value, etc. However, the Pre-Injection Timer is the sum $(t_{pn}(k)+t_{qn}(k))$ and is determined on every iteration of the steps shown in FIG. 8B (e.g., see Step 229 of the method 260), since this value is, in each iteration, compared to a prior maximum value.

Figure 3:
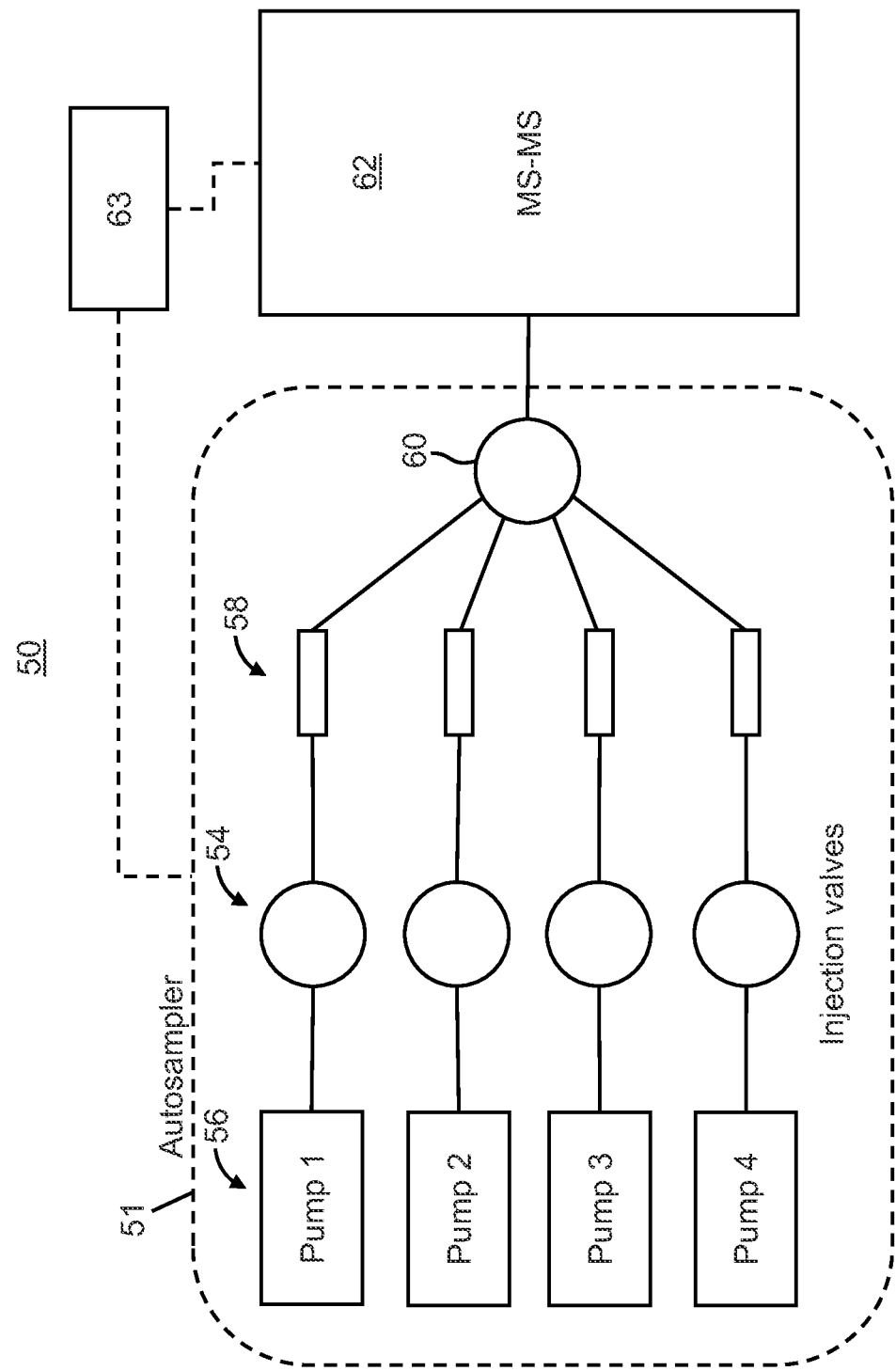
FIG. 3 illustrates in schematic view a known multi-column chromatography system.
Figure 4:
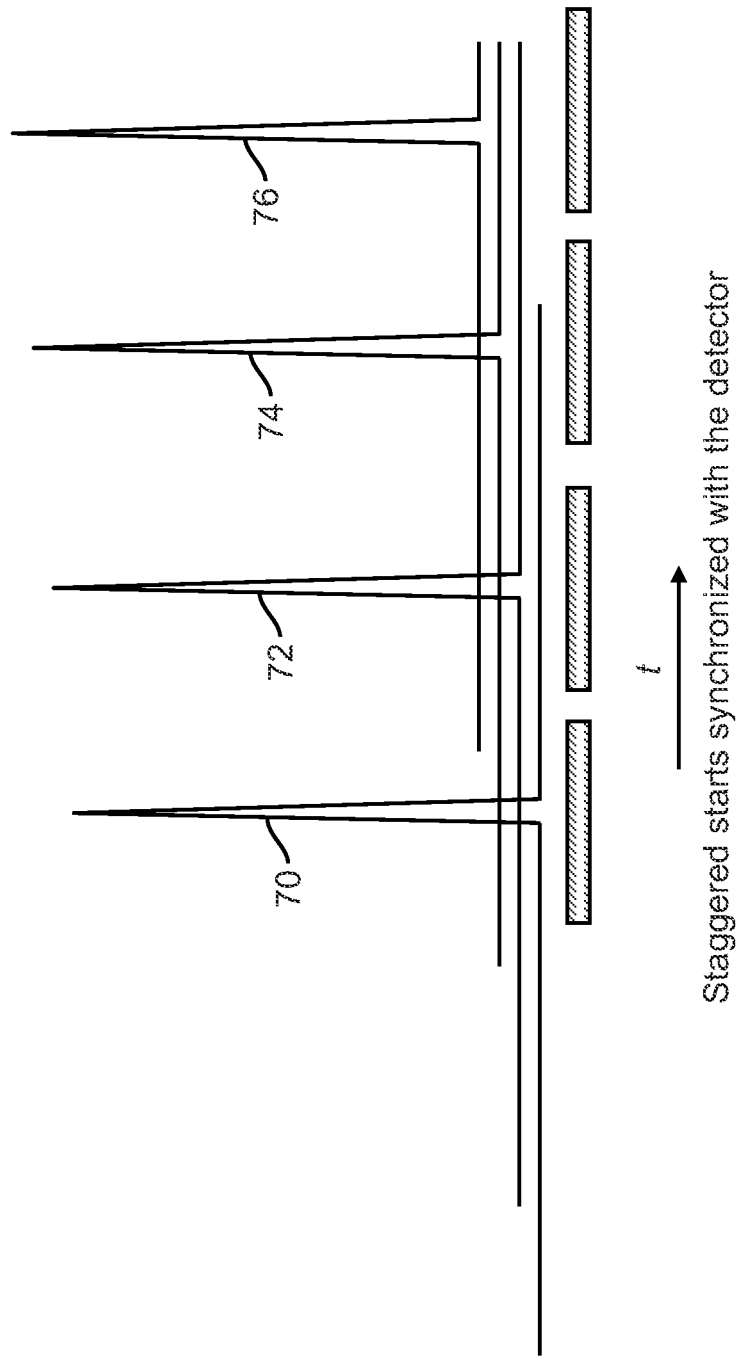
FIG. 4 illustrates the typical results of the multi-column chromatography system of FIG. 2.
Figure 8C:
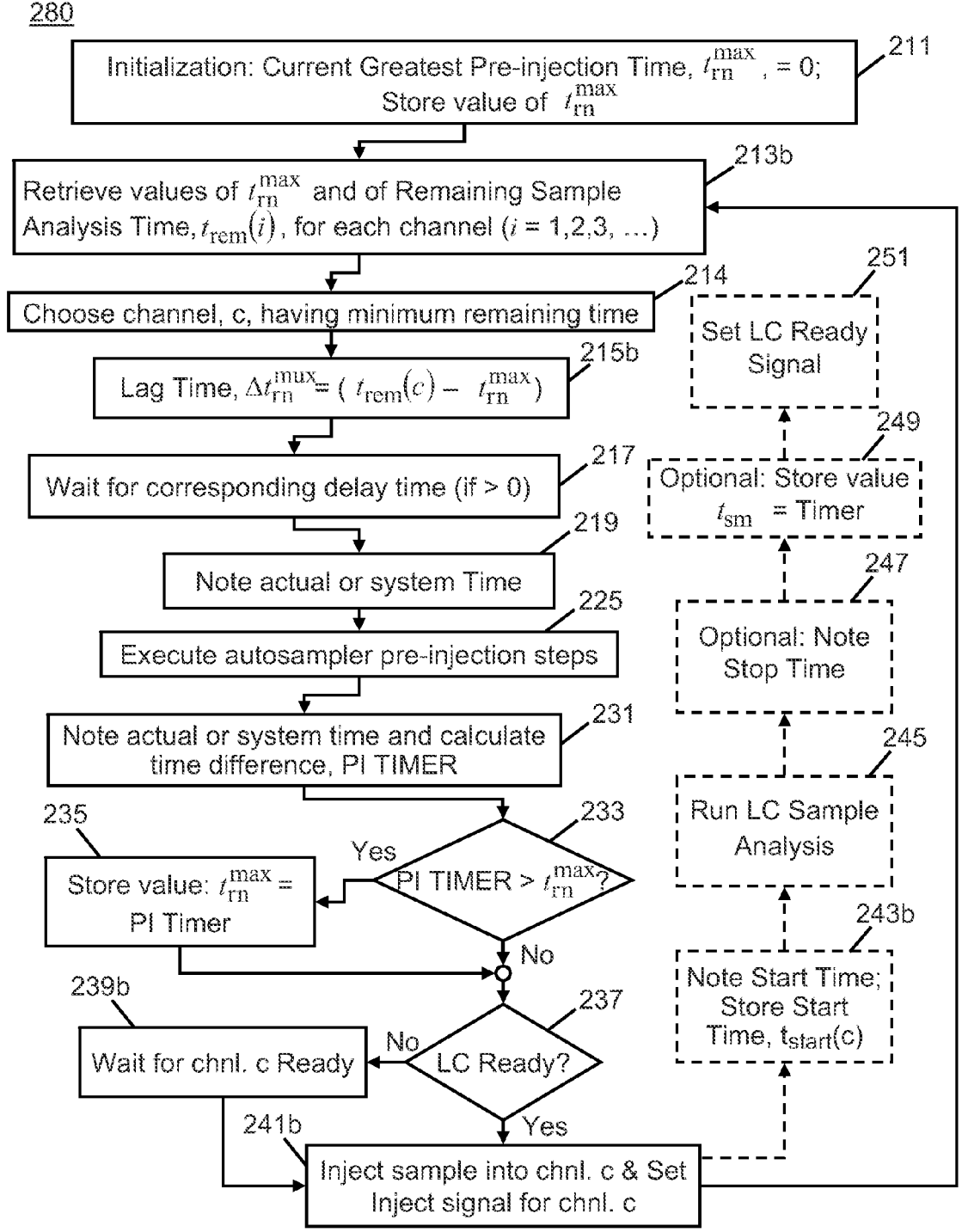
FIG. 8C is a flow diagram of a method for optimizing the operation of an autosampler and a multiplexed LC system in accordance with the present teachings.

For use with a multiplexed LC system comprising several channels, such as the four channels illustrated in FIG. 3, the method shown in FIG. 8A may be slightly modified. A flow diagram of an appropriately modified method, in accordance with the present teachings, in illustrated in FIG. 8C. Steps 211, 217-237 and 245-251 of the method 280 illustrated in FIG. 8C are identical to the correspondingly numbered steps of the method 210 illustrated in FIG. 8A and are thus not re-described. However, the previously described Steps 213, 215, 239, 241 and 243 are modified, in FIG. 8C, to Steps 213b, 215b, 239b, 241b and 243b and a new Step 214 is inserted between Step 213b and Step 215b.

The first step, Step 211, of the method 280 is an initialization step in which, as in the earlier described method 210, the Current Greatest Pre-injection Time for the $n^{th}$ analytical procedure, $t_n^{max}$, is set to zero and stored in the timing database. However, in the next step, Step 213b, the method retrieves the remaining sample analysis time $t_{rem}(i)$, for each ith chromatographic channel. For example, considering the system 50 illustrated in FIG. 3 as a multiplexed LC system, it may be observed that the system comprises four parallel channels, each channel including a pump 56, an injection valve 54 fluidically coupled to the pump and a column 58 fluidically coupled to the injection valve. Thus, when utilized in conjunction with the multiplexed system 50, step 213b would retrieve the four values $t_{rem}(1)$, the time remaining to complete the sample analysis procedure currently being executed on the first channel, as well as $t_{rem}(2)$, $t_{rem}(3)$ and $t_{rem}(4)$, which are the times similarly remaining with regard to the second, third and fourth channels. These time-remaining values may be determined from the formula $t_{rem}(i)=t_s(i)-[t-t_{start}(i)]$ where $t_s(i)$ is the estimated total required sample analysis time for the sample analysis procedure currently being executed on the $i^{th}$ channel, $t_{start}(i)$ is the time at which that analysis procedure was begun (stored in memory or a database in Step 243b or, optionally, in Step 241b) and t is the actual clock time or system time. Alternatively, an estimated analysis-end time, $t_{end}(i)$, for each channel may be stored in memory or a database in Step 243b or, optionally, in Step 241b and the time-remaining values may be determined from the formula $t_{rem}(i)=t_{end}(i)-t$.

In the next step, Step 214, of the method 280 (FIG. 8C), a particular channel is chosen to receive the injection of the next sample, the chosen channel, having channel index, c, being the one that will be available at the soonest time—that is, the channel associated with the minimum remaining time to completion of the currently executing sample analysis procedure. In the next step, Step 215b, the autosampler delay time is calculated using the time-remaining value for the soonest-available channel. Later in the method, in Step 241b, the sample aspirated by the autosampler is injected into channel c, possibly after waiting for this channel to be available in Step 239b.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the spirit, scope and essence of the invention. Neither the description nor the terminology is intended to limit the scope of the invention. All patent application disclosures, patent application publications or other publications are hereby explicitly incorporated by reference herein as if fully set forth herein.

What is claimed is:

1. A method for optimizing the operation of an autosampler coupled to a liquid chromatography (LC) system, comprising:

reading, from a database on an electronic memory storage device, a pre-injection time value corresponding to the time required for the autosampler to perform preparatory operations pertaining to the performing of a sample analysis procedure on a sample and including at least moving a syringe into position over a sample container and drawing the sample from the sample container into the syringe;

calculating an autosampler delay time from the pre-injection time value, a start time of a previously-started sample analysis and a duration time value of the previously-started sample analysis;
performing the autosampler preparatory operations after delaying said autosampler preparatory operations for a time corresponding to the autosampler delay time;
measuring a time value of the preceding performing of autosampler preparatory operations;
replacing the pre-injection time value stored in the database with the measured time value of the preceding performing of autosampler preparatory operations if the measured time value of the preceding performing of autosampler preparatory operations is greater than the pre-injection time value stored in the database; and
injecting the sample from the autosampler into an injection port of the LC system after receipt of a signal from the LC system by the autosampler.

2. A method as recited in claim 1, wherein the pre-injection time value corresponds to the time required for the autosampler to perform preparatory operations including the moving of the syringe into position over the sample container and the drawing the sample from the sample container into the syringe and further including washing of the syringe and the injection port.

3. A method as recited in claim 1, wherein the pre-injection time value corresponds to the time required for the autosampler to perform preparatory operations including the moving of the syringe into position over the sample container and the drawing the sample from the sample container into the syringe and further including transporting of the syringe with the drawn sample to the injection port.

4. A method as recited in claim 1, wherein the read pre-injection time value is one of a plurality of pre-injection time values stored in the database, each stored pre-injection time value corresponding to a different respective sample analysis procedure.

5. A method as recited in claim 1, wherein the reading of the pre-injection time comprises reading, from the database on the electronic memory storage device, a pre-sample time value and a sample transport time value, wherein the time required for the autosampler to perform preparatory operations is the sum of the pre-sample time and the sample transport time.

6. A method as recited in claim 5, the measuring of the time value of the performing of autosampler preparatory operations comprises:
measuring a first time component during which the autosampler performs all preparatory operations prior to the drawing of the sample from the sample container;
measuring a second time component during which the autosampler performs all remaining preparatory operations prior to injecting the sample into the injection port; and
replacing the pre-sample time value and the sample transport time value stored in the database with the measured first and second time components, respectively,
wherein the sum of the first and second time components is equal to the time value of the performing of autosampler preparatory operations.

7. A method as recited in claim 1, further including, prior to the calculating the autosampler delay time from the pre-injection time value and from a sample analysis time value:
reading the sample analysis time value from the database on the electronic memory storage device.

8. A method as recited in claim 7, wherein the read sample analysis time value is one of a plurality of sample analysis time values stored in the database, each of said sample analysis time values corresponding to a different respective sample analysis procedure.

9. A method as recited in claim 7, further comprising:
performing an LC analysis of the injected sample using the LC system; and
replacing the sample analysis time value stored in the database with a measured value of a time required for the LC system to perform the LC analysis.

10. A method as recited in claim 1, wherein the delaying of the autosampler preparatory operations occurs after the operation of autosampler post-injection operations pertaining to the previously-started sample analysis.

11. A method for optimizing the operation of an autosampler coupled to a liquid chromatography (LC) system com having a plurality of simultaneously operating LC channels, the method comprising:
reading, from a database on an electronic memory storage device, a pre-injection time value pertaining to the performing of a sample analysis procedure on a sample and corresponding to the time required for the autosampler to perform preparatory operations including at least moving a syringe into position over a sample container and drawing a sample from the sample container into the syringe;
retrieving or calculating a respective remaining sample analysis time for each of the plurality of LC channels;
calculating an autosampler delay time from the pre-injection time value and from a minimum value of the remaining sample analysis times;
performing the autosampler preparatory operations after delaying said autosampler operations for a time corresponding to the autosampler delay time;
measuring a time value of the preceding performing of autosampler preparatory operations;
replacing the pre-injection time value stored in the database with the measured time value of the preceding performing of autosampler preparatory operations if the measured time value of the preceding performing of autosampler preparatory operations is greater than the pre-injection time value stored in the database; and
injecting the sample from the autosampler into an LC channel that corresponds to the minimum value of the remaining sample analysis times after receipt of a signal from the LC system by the autosampler.

12. A method as recited in claim 11, wherein the pre-injection time value corresponds to the time required for the autosampler to perform preparatory operations including the moving of the syringe into position over the sample container and the drawing the sample from the sample container into the syringe and further including washing of the syringe and the injection port.

13. A method as recited in claim 11, wherein the pre-injection time value corresponds to the time required for the autosampler to perform preparatory operations including the moving of the syringe into position over the sample container and the drawing the sample from the sample container into the syringe and further including transporting of the syringe with the drawn sample to the injection port.

14. A method as recited in claim 11, wherein the reading of the pre-injection time comprises reading, from the database on the electronic memory storage device, a pre-sample time value and a sample transport time value, wherein the time required for the autosampler to perform preparatory operations is the sum of the pre-sample time and the sample transport time.

15. A liquid chromatography system comprising:
a liquid chromatograph (LC) configured to analyze liquid samples;
an LC control process electrically coupled to the LC;
an autosampler configured to inject liquid samples to the LC;
an autosampler control process electrically coupled to the autosampler; and
a computer-readable memory module electrically configured so as to provide data to and receive data from each of the LC control process and the autosampler control process,
wherein the autosampler control process is configured to:
cause the austosampler to perform pre-sampling operations pertaining to and transport operations upon a sample in accordance with a sample analysis procedure after delaying operation for a time corresponding to a calculated autosampler delay time;
measure a time value of the performing of the pre-sampling and transport operations;
cause the autosampler to inject the sample into an injection port of the LC after receipt of a signal from the LC; and
wherein one of the LC control process and the autosampler control process is configured to:
read, from a database on the computer-readable memory module, a pre-injection time value comprising a previously measured time required for the autosampler to perform the pre-sampling and transport operations;
calculate the autosampler delay time from the read pre-injection time value, a start time of a previously-started LC sample analysis and a duration time value of the previously-started LC sample analysis;
replace the pre-injection time value stored in the database with the measured time value of the performing of the pre-sampling and transport operations if the measured value of the performing of the pre-sampling and transport operations is greater than the pre-injection time value stored in the database.

16. A liquid chromatography system as recited in claim 15:
wherein the LC comprises a plurality of LC channels, each channel having a respective LC injection port and configured to perform a different respective LC sample analysis, and the plurality of LC channels configured to perform the LC sample analyses concurrently, and
wherein the autosampler control process is further configured to cause the autosampler to inject the sample into the injection port of an LC channel associated with a minimum remaining sample analysis time.

* * * * *